US006648828B2

(12) United States Patent
Friedman et al.

(10) Patent No.: US 6,648,828 B2
(45) Date of Patent: Nov. 18, 2003

(54) CONTINUOUS, NON-INVASIVE TECHNIQUE FOR MEASURING BLOOD PRESSURE USING IMPEDANCE PLETHYSMOGRAPHY (75) Inventors: Bruce A. Friedman, Tampa, FL (US); Richard Medero, Tampa, FL (US); Lawrence T. Hersh, Tampa, FL (US); Sai Kolluri, Tampa, FL (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 0 days.

(21) Appl. No.: 09/683,916

(22) Filed: Mar. 1, 2002

(65) Prior Publication Data

US 2003/0167012 A1 Sep. 4, 2003

(51) Int. Cl.[7] .................................................. A61B 5/02
(52) U.S. Cl. ........................ 600/506; 600/547; 600/485
(58) Field of Search ................................. 600/506, 507, 600/505, 504, 547, 481, 485, 486, 500, 501, 502

(56) References Cited

U.S. PATENT DOCUMENTS

| 4,349,034 A | | 9/1982 | Ramsey, III |
| 4,360,029 A | | 11/1982 | Ramsey, III |
| 4,425,920 A | | 1/1984 | Bourland et al. |
| 4,543,962 A | | 10/1985 | Medero et al. |
| 4,638,810 A | | 1/1987 | Ramsey, III et al. |
| 4,676,253 A | * | 6/1987 | Newman et al. ............ 600/506 |
| 4,807,638 A | * | 2/1989 | Sramek ...................... 600/485 |
| 4,869,261 A | | 9/1989 | Penaz |
| 4,873,987 A | | 10/1989 | Djordjevich et al. |
| 4,889,133 A | | 12/1989 | Nelson et al. |
| 4,949,710 A | | 8/1990 | Dorsett et al. |
| 5,178,154 A | | 1/1993 | Ackmann et al. |
| 5,309,916 A | | 5/1994 | Hatschek |
| 5,590,662 A | | 1/1997 | Hersh et al. |
| 5,649,543 A | | 7/1997 | Hosaka et al. |
| 5,785,659 A | | 7/1998 | Caro et al. |
| 5,865,755 A | | 2/1999 | Golub |
| 6,186,953 B1 | | 2/2001 | Narimatsu |
| 6,228,033 B1 | * | 5/2001 | Koobi et al. ................ 600/483 |

* cited by examiner

Primary Examiner—Max F. Hindenburg
Assistant Examiner—Navin Natnithithadha
(74) Attorney, Agent, or Firm—George E. Haas; Quarles & Brady LLP (57) ABSTRACT Blood pressure is measured using the pulse transit time required for the blood volume pulse to propagate between two locations in an animal. Impedance plethysmography is employed to detect when the blood volume pulse occurs at one location. The plethysmograph may detect thoracic impedance to determine when the aortic heart valve opens or it may detect impedance at one location on a limb of the animal. Occurrence of the blood volume pulse at another location can be determined by impedance plethysmography or another technique, such as pulse oximetry. The calculation of cardiac stroke volume can be employed to compensate the derivation of the blood pressure for effects due to blood vessel compliance. A nonblood pressure monitor may periodically provide a reference blood pressure measurement that is used calibrate derivation of the blood pressure based on the pulse transit time.

25 Claims, 4 Drawing Sheets

CONTINUOUS, NON-INVASIVE TECHNIQUE FOR MEASURING BLOOD PRESSURE USING IMPEDANCE PLETHYSMOGRAPHY

BACKGROUND OF THE INVENTION

The invention generally relates to apparatus and methods for measuring blood pressure in animals, and more particularly continuous nonblood pressure measurement apparatus and methods.

In the case of a hospitalized patient, it is frequently desired to be able to measure the blood pressure on a continuous basis. A very reliable technique for continuously measuring blood pressure is to insert a saline filled catheter through the patient's vascular system to the point at which it is desired to perform the measurements. The catheter is connected to a pressure sensor, which measures the pressure in the vessel. An alternative method uses a catheter with a pressure sensor at the tip that directly senses the blood pressure. However these techniques involve making an incision through the patient'skin and inserting the catheter into a blood vessel. As a consequence, this invasive procedure entails some risk of complications for the patient.

An indirect, non-invasive process for continuously measuring blood pressure is based on the pulse transit time (PTT) which is the time required for a blood pressure pulse from the heart beat to propagate between two points in the vascular system. One apparatus for this technique includes an electrocardiograph which senses electrical signals in the heart to provide an indication when a blood pulse enters the aorta. A pulse oximeter is placed on an index finger of the patient to detect when the blood pressure pulse reaches that location. The pulse transit time between the heart and the index finger is measured and calibrated to the existing blood pressure that is measured by another means, such as by the automated oscillometric method. Thereafter changes in the pulse transit time correspond to changes in the blood pressure. Generally the faster the transit time the higher the blood pressure. Thus changes in the pulse transit time can be equated to changes in the blood pressure.

However, the electrocardiograph (ECG) senses electrical signals in the heart, which do not indicate the point in time when the blood pressure pulse actually leaves the heart upon the mechanical opening of the aortic valve. A time interval of varying length, known as the cardiac preperiod (PEP), exists between peaks of the QRS wave of the electrocardiogram signal and the aortic valve opening. The inability of prior pulse transit time based monitors to account for the cardiac pre-injection period resulted in an inaccurate measurement of the pulse transit time and thus blood pressure.

In addition changes in the compliance of the blood vessels also affects the pulse transit time. Chronic changes in arterial compliance occur due to aging, arteriosclerosis, and hypertension. Arterial compliance can also change acutely due to neural, humoral, myogenic or other influences. Previous monitoring systems have been unable to separate changes due to compliance from changes due to blood pressure. As a consequence, some degree of inaccuracy exists in calculating blood pressure from the variation of the pulse transit time.

Thus there is a desire to provide a more accurate continuous, non-invasive blood pressure measurement technique.

SUMMARY OF THE INVENTION

An apparatus for continuously and non-invasively monitoring blood pressure includes a device that measures impedance at a first location in the animal. The resultant impedance measurements are employed to detect when a blood pressure pulse occurs at the first location. A sensor is provided to detect when a blood pressure pulse occurs at a second location in the animal. A timer, that is connected to the device and to the sensor, measures the interval of time, which elapses between when blood pressure pulses occur at the first and second locations. A processor employs conventional pulse transit time analysis techniques to derive the blood pressure of the animal from the interval of time measured by the timer.

In one embodiment of the present invention an impedance cardiograph is employed to measure the thoracic impedance of the animal. Analysis of the thoracic impedance measurement determines when the aortic valve of the animal's heart opens, thereby emanating a blood pressure pulse from that first location. A pulse oximeter can be used as the sensor to detect when a blood pressure pulse occurs at a second location in the animal.

In another embodiment, an impedance plethysmograph measures the impedance at two locations on a limb of the animal to detect when a blood pressure pulse occurs at those locations.

Other aspects of the present invention involve use of an electrocardiograph, which along with the impedance cardiograph enables calculation of the cardiac stroke volume. The cardiac stroke volume then is employed to compensate the blood pressure derivation for effects due to blood vessel compliance. In addition, a non-continuous blood pressure monitor can be periodically activated to produce a reference blood pressure measurement that is used to calibrate the pulse transit time analysis.

DETAILED DESCRIPTION

Figure 1:
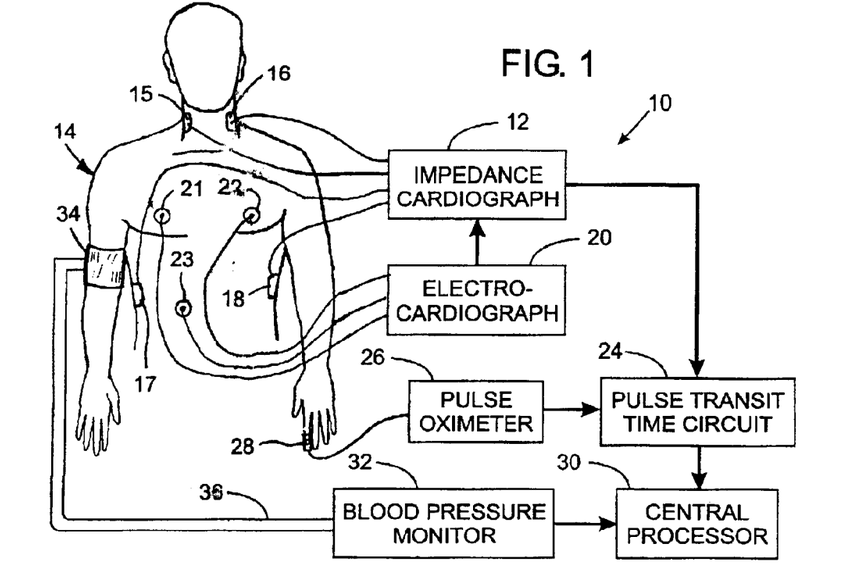
FIG. 1 is a block diagram of a first embodiment of an apparatus according to the present invention.

With initial reference to FIG. 1, a patient monitor 10 comprises a number of systems, which provide medical personnel with information regarding different physiological functions of a patient 14. Specifically the patient monitor 10 includes an impedance cardiograph 12, an electrocardiograph 20, a pulse oximeter 26, and a nonblood pressure monitor 32.

The impedance cardiograph 12 may be based on any of several conventional apparatuses, such as the one described in U.S. Pat. No. 5,178,154. The impedance cardiograph 12 is connected to a patient 14 by four electrode patches 15, 16, 17 and 18, each containing a pair of electrodes that contact the patient's skin. Two of the electrode patches 15 and 16 are placed on opposite sides of the patient's neck, while the remaining pair of electrode patches 17 and 18 are located on opposite sides of the thorax. As an alternative, separate bands each having a pair of strip electrodes can be placed around the patient's neck and thorax.

The output of a high frequency (e.g. 60 kHz) oscillator within the impedance cardiograph 12 is applied between an electrode of each neck electrode patch 15 and 16 and an electrode on each thorax electrode patch 17 and 18. This connection injects a constant current signal of relatively low amperage through the patient 14, thereby establishing a series of equipotential surfaces within the patient which transverse the longitudinal axis of the thorax. A sensing amplifier in the impedance cardiograph 12 is coupled to the other electrode of the four electrode patches 15, 16, 17 and 18 and produces an output signal which corresponds to the voltage established between the neck and thorax as a result of the high frequency excitation signal. Since the excitation current is constant, the sensed voltage is proportional to the thoracic impedance (Z) of the patient 14.

Figure 2:
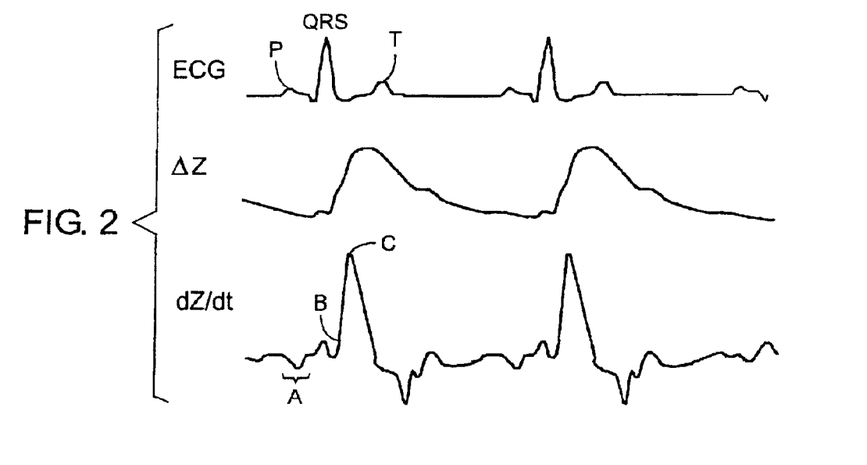
FIG. 2 is a set of waveforms representing signals for an electrocardiogram, change in thoracic impedance and the first derivative of the thoracic impedance.

Changes in the baseline thoracic impedance are related to changes of the intravascular and extravascular fluids within the patient's chest. Variation of the thoracic impedance correlates closely with alterations of central blood volume. Thus information concerning cardiac activity, such as cardiac output, can be obtained from analysis of the first derivative of the thoracic impedance. FIG. 2 illustrates exemplary waveforms for thoracic impedance (Z) and the first derivative (dZ/dt) of the thoracic impedance. The first derivative waveform contains a section A which represents contraction of the atrium of the heart, and a fiducial point B corresponding to the time at which the aortic valve mechanically opens. Peak C corresponds to the maximum blood flow from the left ventricle into the aorta. As a consequence, analysis of the first derivative waveform can be used to identify a point in time at which a pressure pulse emanates from the heart into the vascular system.

Returning to FIG. 1, three conventional electrocardiograph patch electrodes 21, 22 and 23, are positioned on the patient's chest to sense electrical signals within the heart. These electrodes 21–23 are connected to inputs of a conventional electrocardiograph 20 which produces an output that is applied as an input to impedance cardiograph 12. The electrocardiograph 20 senses the ECG waveform illustrated in FIG. 2. Data from the electrocardiograph 20 is used to validate the input signal from electrodes 15, 16, 17 and 18, and also enables the impedance cardiograph 12 to calculate the ventricular stoke volume and cardiac output for the patient. The values of these parameters are supplied to the central processor 30.

With respect to measurement of blood pressure, the impedance cardiograph 12 provides an output signal which indicates the point in time at which the patient's aortic heart valve opens sending a blood pulse into the vascular system. This signal is applied as an input to a standard pulse transit time circuit 24. The pulse transit time circuit 24 also receives an output signal from a conventional pulse oximeter 26 which has an input connected to a conventional probe 28 attached to an index finger of the patient 14. The probe 28 produces a signal that is interpreted by the pulse oximeter 26 to determine when a blood pressure pulse occurs at the finger. In response, the pulse oximeter 26 indicates that pulse event to the pulse transit time circuit 24.

The pulse transit time circuit 24 measures the time interval between the opening of the aortic valve of the patient's heart, as indicated by the signal received from the impedance cardiograph 12, and the arrival of the corresponding blood pressure pulse at the index finger, as indicated by the output signal from the pulse oximeter 26. With additional reference to FIG. 3, the aortic valve opening is indicated by fiducial point G on the waveform for the thoracic impedance derivative (dZ/dt) which is detected by the impedance cardiograph. Another fiducial point H on the pulse oximeter waveform $SpO_2$ indicates the arrival of the pressure pulse at the patient's finger. The time interval PTT between points G and H indicates the diastolic transit time. Another time interval between point G and the peak of the pulse oximeter waveform corresponds to the systolic transit time. Both of these time intervals are measured by the pulse transit time circuit 24 and applied to an input of a central processor 30 of the patient monitor 10.

The central processor 30 is a computerized device which includes a microprocessor, a memory, and input and output circuits. The memory stores software programs that are executed by the microprocessor and stores data used in the execution of those programs. The input and output circuits couple the central processor to other components of the patient monitor. The central processor 30 also includes a control panel and display by which the medical personnel interface which the patient monitor 10.

The central processor 30 calculates the blood pressure from the pulse transit time. To enable this calculation, the pulse transit time for the particular patient has to be correlated to the blood pressure. For that purpose, the central processor 30 receives blood pressure readings from a conventional automatic oscillometeric blood pressure monitor 32, such as the one described in U.S. Pat. No. 4,360,029.

With continuing reference to FIG. 1, the automatic blood pressure monitor 32 is connected to an inflatable cuff 34 by a flexible tube 36. When in use, the inflatable cuff 34 is wrapped around an arm of the patient 14. The blood pressure monitor 32 periodically (e.g. every 30 minutes) activates an internal pump which inflates the cuff 34 to a predefined pressure which is known to occlude the flow of blood within the blood vessels of the patient's arm 14. For example, if previous pressure measurements have been taken from this patient, the occlude pressure may be a predefined amount (e.g. 60 mm of mercury) greater than the previously determined systolic pressure. The blood pressure monitor 32 has a pressure transducer which produces an electrical signal that indicates the pressure in the cuff.

Once this occlude pressure has been obtained, a controlled deflation of the cuff 12 occurs while the pressure therein is being measured. As is conventional practice, the cuff gradually deflates in a series of steps with the nominal pressure at each step being referred to as the "deflation step pressure". The instantaneous pressure at each step oscillates slightly due to the force exerted on the cuff 12 by the blood pulsing through the patient's blood vessels. These pressure oscillations are superimposed on the deflation step presure. The blood pressure monitor senses the pressure oscillations and employs that data to derive values for the patient's systolic pressure, diastolic pressure, and mean arterial pressure using well known techniques.

The pulse transit time (PTT) is related to the blood pressure (BP) according to the expression $BP=\alpha(PTT)^{-\gamma}+\beta$ where $\gamma$ is a positive number. There is a correlation between the volumetric elasticity (compliance) of the blood vessel and the $\alpha$ term. There is a further correlation between the volumetric elasticity and the pulse transit time at a constant blood pressure level. Hence, there is a relationship between the value of α and the pulse transit time. Thus the value of α can be determined as a function of the pulse transit time. The value for β is determined by solving the above expression using a measurement from the non-continuous blood pressure monitor 32 and a pulse transit time value from the pulse transit time circuit 24. Thereafter, the patient's systolic and diastolic blood pressures can be determined from measurement of the corresponding pulse transit times. However, periodically the blood pressure monitor 32 is activated to acquire another oscillometeric blood pressure measurement which is then used to recalibrate the continuous blood pressure measurement that is based on the pulse transit time.

Alternatively, the complexity of the patient monitor 10 can be reduced by eliminating the nonblood pressure monitor 32 and requiring that medical personnel periodically obtain the a blood pressure measurement, such as by the conventional manual auscultatory method. That blood pressure measurement then would be entered into the control panel of the central processor 30 to calibrate the continuous blood pressure measurement that uses the pulse transit time.

The present continuous blood pressure monitoring technique has greater accuracy than prior pulse transit time based devices, because of the use of impedance cardiography to determine when the pressure pulse actually emanates from the heart. This eliminates errors due to variation of the cardiac pre-injection period in those prior monitors that relied on ECG signals to indicate the emanating pulse.

In addition, the cardiac stroke volume determined by the impedance cardiograph is employed by the central processor 30 to compensate for changes in pulse transit time due to the compliance of the blood vessels. If the compliance of the blood vessels remain constant, then change in blood pressure would result in a corresponding variation in pulse transit time. However, the vascular compliance can change, which will confound the relationship between blood pressure and pulse transit time. It is also known that if the vascular compliance is constant, increases in stroke volume will result in increases in blood pressure. If the relationship between stroke volume and blood pressure changes (as measured at calibration) then it can be concluded that the compliance has changed. This can therefore be used to adjust the relationship between pulse transit time and blood pressure.

Figure 4:
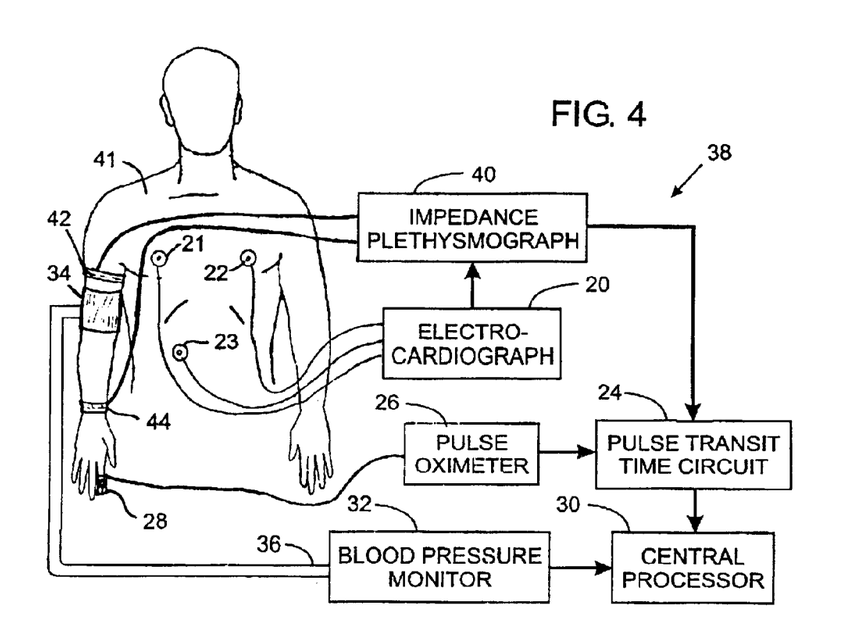
FIG. 4 block diagram of a second embodiment of an apparatus according to the present invention.

FIG. 4 illustrates an alternative embodiment of an apparatus for measuring blood pressure according to the present invention. The apparatus 38 is similar to the embodiment in FIG. 1 and identical components have been given the same reference numerals. The primary difference is that the second embodiment does not utilize an impedance cardiograph. Instead, the latter apparatus 38 employs an impedance plethysmograph 40 which senses the impedance at two locations on an arm of the patient 41. For that purpose, a first electrode band 42 is placed around the upper portion of the patient's arm and a second electrode band 44 is placed around the wrist of that arm. Each band 42 and 44 has an electrode, between which the high-frequency excitation signal is applied, and a pair of voltage sensing electrodes which are connected to separate sensing amplifiers in impedance plethysmograph 40.

Figure 5:
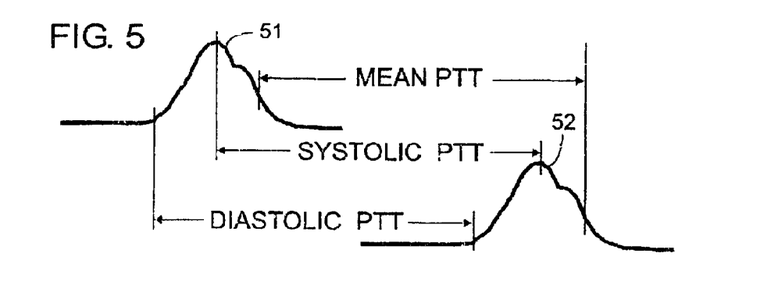
FIG. 5 depicts signal waveforms used by the second embodiment.

The impedance plethysmograph 40 operates in a similar manner to the impedance cardiograph described previously in that the plethysmograph measures the impedance of the patient's arm at each location where one of the electrode bands 42 and 44 is located. Those impedances vary as blood pulses through the arteries and veins beneath the respective electrode band. The impedance plethysmograph 40 produces a separate electrical signal when the blood pressure pulse reaches the location of the first and second electrode bands 42 and 44 as shown in FIG. 5. Note that in this embodiment fiducial points on the waveforms are employed to derive the systolic pressure using the maximum points, the diastolic pressure using the minimum points, and the mean arterial pressure using midpoints of the waveforms.

Therefore the pulse transit circuit 24 receives a signal pulse from the impedance plethysmograph 40 when the blood pulse reaches the first electrode band 42 and another signal pulse when the blood pulse reaches the second electrode band 44. The pulse transit time circuit 24 responds by measuring the time interval between the receipt of these signal pulses. This time interval is used in the same manner as the time interval in the patient monitor 10 in FIG. 1 to determine the blood pressure.

The impedance plethysmograph also provides a heartbeat-to-heartbeat measure of the arm blood volume changes which can be used as an estimate of changes in the blood vessel compliance in that limb. In other words, the blood volume of the arm should vary by the same amount during each cardiac cycle, if the blood pressure remains constant. Any change in that blood volume variation would be due to a change in the compliance of the blood vessels which thus can be quantified and used as a compensation factor in the calculation of blood pressure by the central processor 30.

Figure 3:
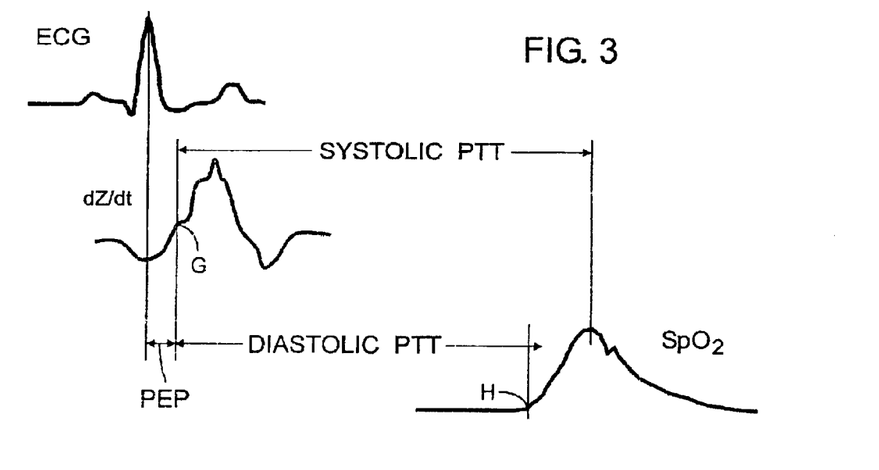
FIG. 3 is a graph depicting the relationship among the electrocardiograph signal, the first derivative of the thoracic impedance cardiograph, and a pulse oximeter signal.
Figure 6:
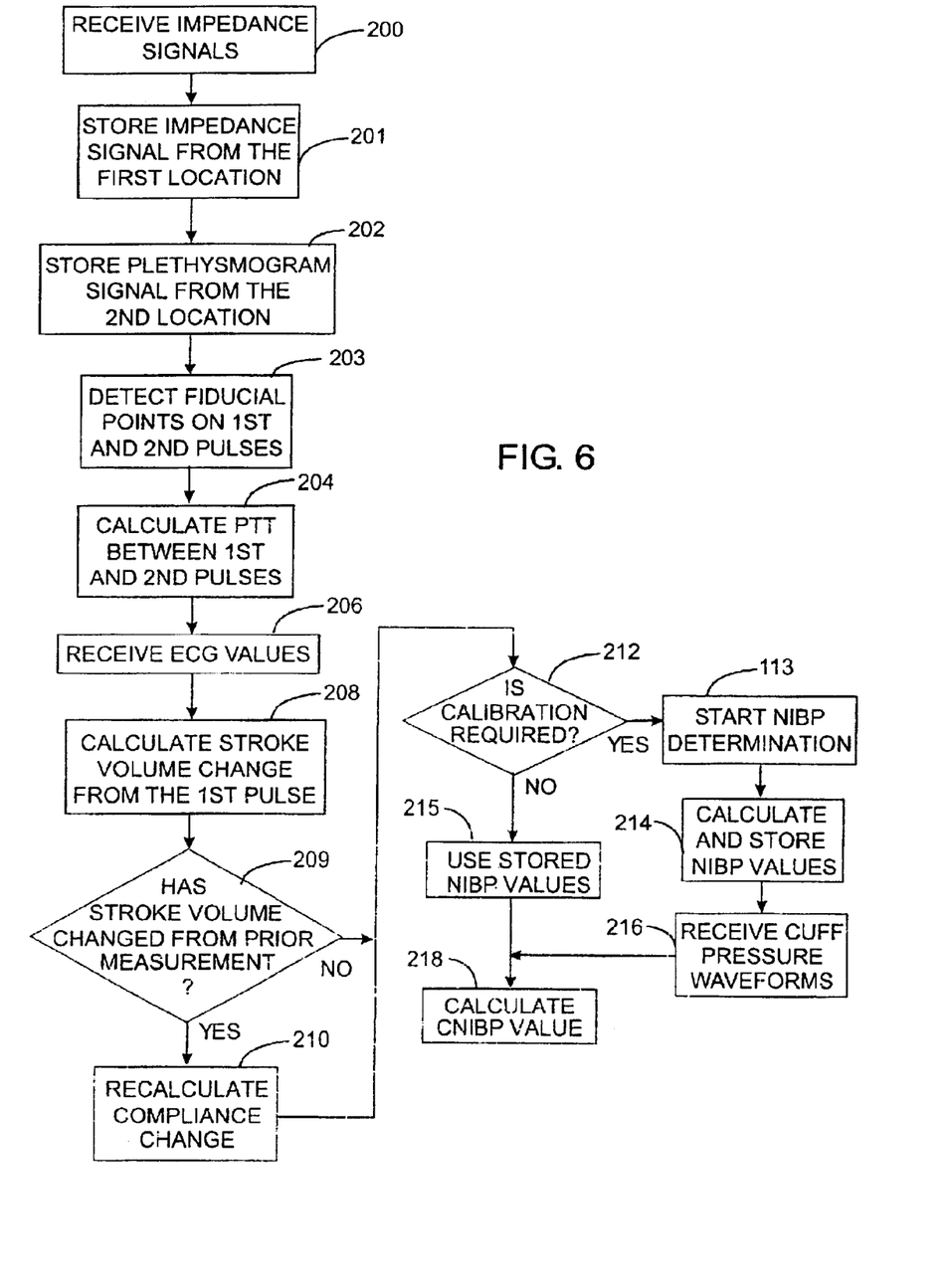
FIG. 6 is a flowchart of a first blood pressure measurement process.

FIG. 6 is a flow chart of a first blood pressure measurement process according to the invention which commences at step 200 with the receipt of the thoracic impedance signal from the impedance cardiograph 12 which is stored at step 201 The signal produced by the pulse oximeter monitor 26 and probe 28 is stored at step 202. These stored signals are analyzed by selecting the appropriate fiducial point at steps 203 and 204. In the case of diastolic pressure, the selected fiducial point is the aortic valve opening on the impedance cardiograph waveform and the minimum of the blood volume pulse as shown in FIG. 3. Once the fiducial points have been detected, the central processor 30 measures Pulse Transit Time (PTT).

In step 206 the ECG signal is received from electrocardiograph 20 and combined with the impedance signal from the impedance cardiograph 12 to calculate the stroke volume at step 208. If at step 209 the stroke volume has changed, the compliance adjustment is recalculated at step 210, otherwise, the existing compliance adjustment is used.

If blood pressure calibration has not been stored in processor 30, an intermittent blood pressure is activated at step 212. In that case, the process branches to step 213 at which an intermittent nonblood pressure (NIBP) determination commences. At step 214 the NIBP is derived using conventional techniques and then stored. The cuff pressure waveforms then are received at step 216. If recalibration was not required the previously'stored NIBP values are obtained at step 215 Then, the respective data are used at step 216 with the PTT and the compliance adjustment to calculate the continuous nonblood pressure value.

Figure 7:
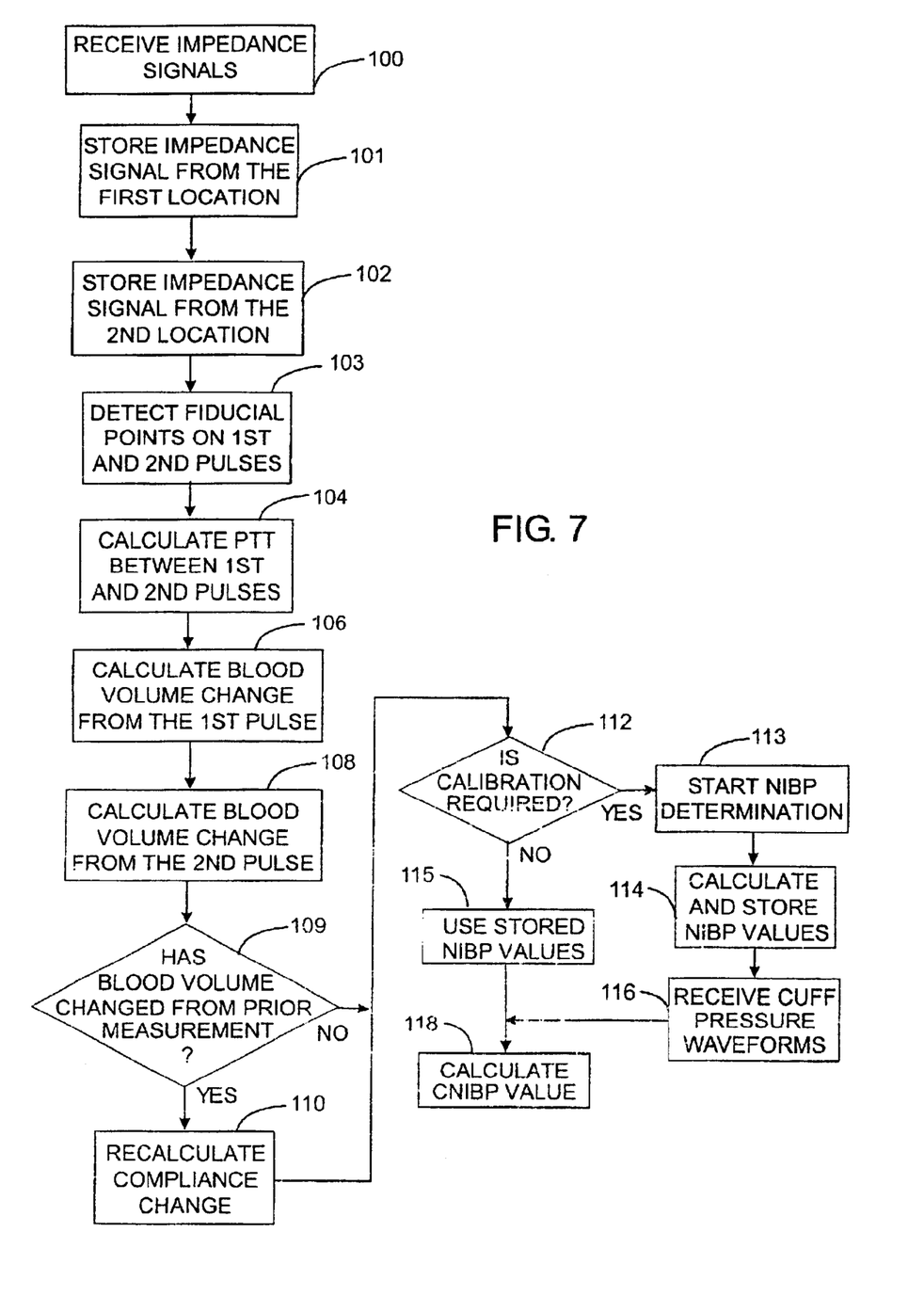
FIG. 7 shows a flowchart of the signal processing for a second embodiment of the invention.

FIG. 7 shows a flow chart of the signal processing for a second embodiment of the invention which commences at step 100 with receipt of impedance signals from the plethysmograph 40. Those signals are stored at steps 101 and 102. The stored signals then are analyzed by selecting the appropriate fiducial point at step 103. To estimate diastolic pressure, the selected fiducial point is the minimum of the blood volume pulses 51 and 52 shown in FIG. 5. Once the fiducial points have been detected, the Pulse Transit Time (PTT) is measured at step 104 by the central processor 30.

Blood volume changes as determined from two impedance pulses at steps 106 and 108 are used to determine the blood volume change for that heart beat. If the blood volume has changed at step 109, the vessel compliance adjustment is recalculated at step 110, otherwise, the existing vessel compliance adjustment is used.

Then at step 112 a determination is made whether the apparatus requires recalibration, as may be necessary at periodic intervals. If recalibration is needed the process branches to step 113 at which a intermittent nonintermittent blood pressure (NIBP) determination commences. At step 114 the NIBP is calculated using conventional techniques and then stored. The cuff pressure waveforms then are received at step 116. If recalibration was not required the previously stored NIBP values are obtained at step 115 Then, the data are used at step 116 with the PTT and the compliance adjustment to calculate the continuous nonblood pressure value.

The foregoing description was primarily directed to a preferred embodiment of the invention. Although some attention was given to various alternatives within the scope of the invention, it is anticipated that one skilled in the art will likely realize additional alternatives that are now apparent from disclosure of embodiments of the invention. Accordingly, the scope of the invention should be determined from the following claims and not limited by the above disclosure.

What is claimed is:

1. An apparatus for continuously and non-invasively monitoring blood pressure in an animal, said apparatus comprising:
    a device which measures impedance of the animal and from that impedance detects when a blood volume pulse is emitted from the heart of the animal;
    a sensor which detects a blood volume pulse occurring at another location in the animal;
    a timer connected to the device and to the sensor, wherein the timer measures an interval of time which elapses between when a blood volume pulse is emitted from the heart and a blood volume pulse occurring at the other location in the animal; and
    a processor which derives the blood pressure of the animal from the interval of time measured by the timer.

2. The apparatus as recited in claim 1 wherein the timer measures an interval of time which elapses between when a blood volume pulse is emitted from the heart and a predefined fiducial point on the blood volume pulse detected by the sensor.

3. The apparatus as recited in claim 2 wherein the predefined fiducial point is a point at which the blood volume pulse has a minimum value, and the blood pressure derived by the processor corresponds to diastolic blood pressure.

4. The apparatus as recited in claim 2 wherein the predefined fiducial point is a point at which the blood volume pulse has a maximum value, and the blood pressure derived by the processor corresponds to systolic blood pressure.

5. The apparatus as recited in claim 2 wherein the predefined fiducial point is a midpoint of the blood volume pulse, and the blood pressure derived by the processor is a mean arterial blood pressure.

6. The apparatus as recited in claim 1 wherein the sensor comprises a pulse oximeter.

7. The apparatus as recited in claim 1 wherein the device comprises an impedance cardiograph that measures thoracic impedance of the animal and determines from the thoracic impedance when a blood volume pulse is emitted from the heart.

8. The apparatus as recited in claim 7 wherein the impedance cardiograph employs the thoracic impedance to determine when the aortic valve of the heart opens.

9. The apparatus as recited in claim 7 further comprising an electrocardiograph connected to the impedance cardiograph thereby enabling measurement of cardiac stroke volume; and wherein the processor employs the measurement of cardiac stroke volume to compensate measurement of the blood pressure for effects due to blood vessel compliance.

10. The apparatus as recited in claim 9 wherein the processor derives the blood pressure (BP) from the interval of time (PTT) according to the expression:

$$BP = \alpha(PTT)^{-\gamma} + \beta$$

where $\alpha$ and $\beta$ are constants for the animal and $\gamma$ is a positive number; and
    employs the measurement of cardiac stroke volume to modify $\alpha$.

11. The apparatus as recited in claim 9 wherein the processor derives the blood pressure (BP) from the interval of time (PTT) according to the expression:

$$BP = \alpha(PTT)^{-\gamma} + \beta$$

where $\alpha$ and $\beta$ are constants for the animal and $\gamma$ is a positive number; and
    employs the measurement of cardiac stroke volume to modify $\beta$.

12. The apparatus as recited in claim 1 wherein the sensor comprises an impedance plethysmograph that measures a given impedance of the animal at the other location, and determines from that given impedance when the blood volume pulse occurs at the other location.

13. The apparatus as recited in claim 1 further comprising a nonblood pressure monitor, which periodically supplies a reference measurement of blood pressure to the processor.

14. The apparatus as recited in claim 13 wherein the processor employs the reference measurement of blood pressure to calibrate derivation of the blood pressure from the interval of time measured by the timer.

15. An apparatus for non-invasively monitoring blood pressure in an animal, said apparatus comprising:
    an impedance cardiograph that measures thoracic impedance of the animal and determines from the thoracic impedance when a blood volume pulse is emitted from the heart;
    electrocardiograph connected to the impedance cardiograph;
    a sensor which detects when a blood volume pulse occurs at a second location in the animal;
    a timer connected to the impedance cardiograph and the sensor, wherein the timer measures an interval of time which elapses between when a blood volume pulse is emitted from the heart and when a blood volume pulse occurs at the second location; and
    a processor which derives tie blood pressure of the animal from the interval of time measured by the timer.

16. The apparatus as recited in claim 15 wherein the sensor measures another impedance at a second location of the animal and determines there from when a blood volume pulse occurs at the second location.

17. The apparatus as recited in claim 15 wherein the sensor comprises a pulse oximeter.

18. The apparatus as recited in claim 15 further comprising a nonblood pressure monitor which periodically supplies a reference measurement of blood pressure to the processor, which employs the reference measurement to calibrate the derivation of the blood pressure of the animal from the interval of time measured by the timer.

19. The apparatus as recited in claim 15 wherein the impedance cardiograph employs information from the electrocardiograph to produce a measurement of stroke volume of the heart in the animal.

20. The apparatus as recited in claim 19 wherein measurement of stroke volume is applied to the processor and wherein the processor employs the measurement of stroke volume to compensate derivation of the blood pressure of the animal for effects due to blood vessel compliance.

21. A method for continuously and non-invasively monitoring blood pressure in an animal having a heart, said method comprising:

measuring thoracic impedance the animal;

determining from the thoracic impedance when a blood volume pulse is emitted from the heart;

detecting a blood volume pulse occurring at another location in the animal;

measuring an interval of time which elapses between when a blood volume pulse is emitted from the heart and occurrence of the blood volume pulse at the other location; and deriving the blood pressure of the animal from the interval of time measured by the timer.

22. The method as recited in claim 21 further comprising:

producing an electrocardiogram waveform representing activity of a heart in the animal;

deriving a cardiac stroke volume measurement in response to the thoracic impedance and the electrocardiogram waveform; and employing the cardiac stroke volume measurement to compensate derivation of the blood pressure of the animal for effects due to blood vessel compliance.

23. The method as recited in claim 21 wherein detecting when a blood volume pulse occurs at a second location comprises measuring an impedance at the second location of the animal.

24. The method as recited in claim 21 further comprising periodically activating a nonblood pressure monitor to produce a reference measurement of blood pressure.

25. The method as recited in claim 24 further comprising calibrating deriving the blood pressure of the animal using the reference measurement of blood pressure.

* * * * *

UNITED STATES PATENT AND TRADEMARK OFFICE
CERTIFICATE OF CORRECTION

PATENT NO. : 6,648,828 B2
DATED : November 18, 2003
INVENTOR(S) : Friedman et al.

It is certified that error appears in the above-identified patent and that said Letters Patent is hereby corrected as shown below:

Column 3,
Line 49, replace "stoke" with -- stroke --.

Column 8,
Line 57, replace "tie" with -- the --.

Signed and Sealed this

Thirteenth Day of July, 2004

JON W. DUDAS
*Acting Director of the United States Patent and Trademark Office*